US006365656B1

(12) United States Patent
Green et al.

(10) Patent No.: US 6,365,656 B1
(45) Date of Patent: Apr. 2, 2002

(54) LIQUID DISPERSION POLYMER COMPOSITIONS, THEIR PREPARATION AND THEIR USE

(75) Inventors: Michael Green; Eleanor Bernice Ridley, both of Huddersfield (GB); Dwayne Erick Gavin, Hazel Crest, IL (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/543,287

(22) Filed: Apr. 5, 2000

Related U.S. Application Data

(60) Provisional application No. 60/128,114, filed on Apr. 7, 1999.

(51) Int. Cl.[7] .......................... C08L 91/00; C08L 37/00; C08L 51/00; A61K 7/06; A61K 31/78
(52) U.S. Cl. .................. 524/313; 523/105; 524/504; 524/531; 424/70.1; 424/78.03
(58) Field of Search .................. 523/105; 524/313, 524/504, 531; 424/70.1, 78.03

(56) References Cited

U.S. PATENT DOCUMENTS

| 4,075,141 A | 2/1978 | Porter, Jr. et al. ......... 260/17.2 |
| 4,528,321 A | 7/1985 | Allen et al. .................. 524/761 |
| 5,004,598 A | * 4/1991 | Lockhead et al. ............ 424/59 |
| 5,084,506 A | * 1/1992 | Faler et al. |
| 5,368,850 A | 11/1994 | Cauwet et al. ................. 424/70 |
| 5,468,801 A | * 11/1995 | Antonelli et al. |
| 5,476,882 A | * 12/1995 | Berner et al. |
| 5,531,993 A | * 7/1996 | Griat .......................... 424/401 |
| 5,585,104 A | 12/1996 | Ha et al. ..................... 424/401 |
| 5,679,328 A | 10/1997 | Dupuis ..................... 424/70.13 |
| 5,711,951 A | 1/1998 | Kopolow .................... 424/401 |

FOREIGN PATENT DOCUMENTS

| WO | 98/09998 | 3/1998 |

OTHER PUBLICATIONS

Chris Holden, Waterborne Polymers, "Formulating Hair and Skin Products More Effectively", pp. 21–23.

* cited by examiner

*Primary Examiner*—Tae H. Yoon
(74) *Attorney, Agent, or Firm*—Kevin T. Mansfield

(57) ABSTRACT

Liquid dispersion polymer compositions which comprise microparticles of a hydrophilic, water soluble or swellable polymer, preferably an acrylic-based polymer, dispersed in a di- or triglyceride oil such as soybean oil and an oil-in-water surfactant, are useful to prepare microparticulate thickening systems to thicken aqueous or aqueous/organic compositions, particularly for use in personal care and pharmaceutical formulations. The preparation and the use of these liquid dispersion polymer compositions is described.

20 Claims, No Drawings

LIQUID DISPERSION POLYMER COMPOSITIONS, THEIR PREPARATION AND THEIR USE

This Application claims benefit of Provisional Application Ser. No. 60/128114 filed Apr. 7, 1999.

FIELD OF THE INVENTION

The present invention relates to liquid dispersion polymer compositions which comprise a dispersed polymer phase, a continuous carrier phase and a surfactant, their preparation and the use of these liquid dispersion polymer compositions to prepare microparticulate thickening systems which thicken aqueous or aqueous/organic compositions. More particularly it relates to liquid dispersion polymer compositions which comprise microparticles of a hydrophilic, water soluble or swellable polymer, preferably an acrylic-based polymer, which is dispersed in a di- or triglyceride oil carrier phase and an oil-in-water surfactant, their preparation and the use of these liquid dispersion polymer compositions to prepare microparticulate thickening systems to thicken aqueous or aqueous/organic compositions, particularly for use in personal care and pharmaceutical formulations.

Thickeners are used extensively in personal care formulations such as cosmetic and pharmaceutical formulations, to affect the aesthetics, product application and suspension and delivery of the active raw materials. Polymeric thickeners have been used for this purpose for many years. The types of polymeric thickeners that have been used range from natural gums such as guar, through modified natural materials such as hydroxyethyl cellulose, to synthetic thickeners such as the Carbomers® based on polyacrylic acids.

The Salcare® range of liquid dispersion polymers, available through Ciba Specialty Chemicals, High Point, N.C., is a range of microparticulate acrylic-based polymeric thickeners in a hydrophobic carrier medium. Salcare® SC91 is an anionic thickening agent based on a sodium acrylate polymer and mineral oil carrier with PPG-1 trideceth-6 as the activator surfactant. Salcare® SC92 is a cationic copolymer thickener and conditioner comprising polyquaternium 32 and mineral oil. Salcare® SC95 and Salcare® SC96 are cationic homopolymer thickeners and conditioners. Salcare® SC95 comprises polyquaternium 37 in mineral oil with PPG-1 trideceth-6. Salcare® SC96 comprises polyquaternium 37 in propylene glycol dicaprylate dicaprate with PPG-1 trideceth-6.

The tiny, spherical microparticles of the above hydrophilic acrylic polymers, whether anionic or cationic in charge, have a typical particle size in the range of 0.1–2 microns, with an average particle size in the range of 0.5–1.0 microns. The polymer microparticles are preferably manufactured by methods in which water soluble vinyl addition monomers are polymerized utilizing a water-in-oil polymerization route.

On stirring of any of the above liquid dispersion polymers into an aqueous system, the activator surfactant converts the hydrophobic carrier into an oil-in-water emulsion. By the term "activator surfactant" is meant a surfactant which activates the conversion of the hydrophobic carrier into an oil-in-water emulsion. At the same time the hydrophilic polymer expands on exposure to water but does not dissolve, resulting in a smooth and rapid viscosity increase. Typically the polymer particles swell to give a microparticulate thickening system comprising polymer particles having a typical particle size in the range of 2.5–5 microns in diameter. Since the water molecules move into the small polymer particles by osmosis, the osmotic effect experienced by the polymer particle is a balance between water and any electrolyte present in the system. Hence high electrolyte levels reduce the swelling of the polymer particles.

The microparticulate thickening systems have a pseudoplastic Theological profile which gives good stability and suspension characteristics at low shear rates (such as those experienced by the product on standing), and low apparent viscosities at high shear rates, which corresponds to excellent rub-in characteristics.

As previously mentioned, the continuous organic carrier phase for the above Salcare® liquid dispersion polymers is either mineral oil or a synthetic glycol ester, propylene glycol dicaprylate dicaprate. Mineral oil is known to provide good barrier properties to the skin. Now however it has been found that liquid dispersion polymer compositions which comprise microparticles of a hydrophilic, water soluble or swellable polymer as the dispersed polymer phase, a di- or triglyceride oil as the continuous organic carrier phase and an oil-in-water surfactant, offer a number of advantages to the personal care end user. Like the known Salcare® liquid dispersion polymers, the inventive liquid dispersion polymers provide microparticulate thickening systems which give effective thickening to aqueous or aqueous/organic personal care formulations at concentrations of 0.1% to 8%, preferably 1% to 6%, by weight. In addition however they combine the thickening effect of the liquid dispersion polymer with the advantages of a cosmetically acceptable di- or triglyceride carrier oil. Thus the resulting oil-in-water microparticulate thickening emulsions provide excellent moisturizing properties and excellent emolliency to skin care formulations, leading to smooth skin with good elasticity. Additionally, since the activator remains outside the swollen particle, other synthetic or natural oils, including silicones, can be readily emulsified without the need for calculation of the HLB, heating, neutralization or use of additional emulsifiers. This means that the thickener can be used to produce personal care emulsions by a very simple room temperature production process in a shorter manufacturing time, and multiple ingredients which may include two phases can be mixed in one vessel prior to addition of the thickener. Additionally, by selection of an appropriate cationic or anionic polymer, thickened compositions which are compatible with a variety of cationic or anionic co-ingredients can be obtained.

SUMMARY OF THE INVENTION

In one aspect the present invention provides a liquid dispersion polymer composition comprising a hydrophilic, water soluble or swellable polymer as a dispersed polymer phase, a di- or triglyceride oil as a continuous organic carrier phase and an oil-in-water surfactant, wherein the polymer is in the form of microparticles having an average particle size in the range of 0.1 to 2 microns.

Typically the liquid dispersion polymer composition comprises
a) from 35% to 65% by weight of the polymer,
b) from 20% to 50% by weight of a di- or triglyceride oil, and
c) from 5% to 25% by weight of a surfactant or a surfactant mixture, each based on the total weight of the composition.

Advantageously the hydrophilic polymer a) is water swellable, i.e. it is sufficiently crosslinked to swell but not dissolve in water. Preferably it is acrylic-based. Also it is preferably anionic or cationic.

The di- or triglyceride oil b) may be of natural or synthetic origin. Preferably it is of animal or plant origin. Most preferably the oil is a naturally occurring triglyceride vegetable oil.

Soybean oil is especially preferred.

The surfactant or surfactant mixture c) is advantageously a mixture of surfactants. Preferably the mixture comprises both surfactants useful in the manufacture of the microparticles of swellable polymer a), and at least one surfactant which serves as the activator for the subsequent oil-in-water microparticulate thickening emulsions. This activator surfactant for the oil-in-water thickening emulsions comprises from 0.5% to 8% by weight of the composition, preferably from 1% to 3% by weight of the composition. It has been found that when the liquid dispersion polymer composition comprises a di- or triglyceride oil as the continuous phase, substantially less of the activator surfactant is needed than with the less polar mineral oil. Preferably the activator surfactant is a nonionic oil-in-water emulsifier having a HLB generally above 10. Suitable emulsifiers of this type are well known to those skilled in the art. Ethoxylated alcohols are preferred, with PPG1-trideceth 6 being especially preferred.

Additionally the composition may contain minor amounts of other components which do not affect its essential characteristics. Typically these other components may include up to about 3% by weight each of water and volatile organic solvents as well as small amounts of other components which are left over from the preparation of the water soluble or swellable polymers.

Advantageously the composition comprises
a) from 40% to 60% by weight of the polymer, wherein the polymer is anionic or cationic and is water swellable,
b) from 25% to 45% by weight of a di- or triglyceride oil, and
c) from 8% to 20% by weight of a surfactant or a surfactant mixture, each based on the total weight of the composition.

A particularly preferred composition comprises
a) from 45% to 58% by weight of the polymer, wherein the polymer is anionic or cationic and is water swellable,
b) from 30% to 40% by weight of a di- or triglyceride oil, and
c) from 10% to 18% by weight of a mixture of surfactants, each based on the total weight of the composition.

A very particularly preferred composition comprises
a) from 45% to 58% by weight of the water swellable polymer, wherein the polymer is anionic and 65% to 85% of the acid groups are in the form of their sodium salt,
b) from 32% to 38% by weight of a triglyceride oil,
c) from 12% to 18% by weight of a mixture of surfactants, each based on the total weight of the composition.

In a most particularly preferred embodiment of the above composition, designated Salcare® AST, the triglyceride oil comprises soybean oil.

Still another aspect of the present invention is the provision of thickened aqueous or watercontaining compositions, in particular personal care formulations, which comprise
a) 0.1% to 8% by weight, preferably 1% to 6% by weight of a liquid dispersion polymer composition as described above,
b) 0.1% to 50%, preferably 2% to 35% by weight of additional ingredients, for example personal care ingredients such as cosmetic or pharmaceutical excipients and/or active ingredients and
c) 45% to 99% of water or a mixture of water and a water-miscible organic solvent such as a lower alcohol.

These compositions may be in the form of lotions, creams, salves, gels or ointments.

The additional components can be any ingredient which may form part of a thickened aqueous emulsion of the oil-in-water type. Non-limiting examples of cosmetic ingredients include: antimicrobials, skin conditioning agents such as acetylated lanolin alcohol, allantoin, aloe vera, acetamide monoethanolamine, myrstyl propionate, dimethicone copolyol, dimethyl polysiloxane, moisturizers, barrier creams, emollients, alpha hydroxy acids such as lactic acid and citric acid, hair conditioners such as amodimethicone, cyclomethicone, panthenol, lauramide diethanolamine, lauramine oxide and silk protein, perfume components, hair dyes and bleaches, UV sun screening agents such as para aminobenzoic acid, octyl salicylate, and octyl methoxycinnamate, "sunless" tanning agents, whitening agents, insect repellents, essential oils such as patchouli oil, peppermint oil, rosemary oil, citronella oil, tea tree oil, orange or lemon oils, cedarwood oil and sandalwood oil, vitamins, and preservatives such as propyl paraben and imidazolidinyl urea. Pharmaceutically active ingredients may vary widely and include all therapeutic agents intended for topical application to the skin or hair, in particular substances to treat itching, tingling, scaling, inflammation or infection of the skin, burns, and scalp hair loss of humans or other mammals.

Still another aspect of the present invention is the provision of a method for the preparation of a therapeutic lotion, cream, salve, gel or ointment which comprises mixing 0.1% to 8% by weight, preferably 1% to 6% by weight of a liquid dispersion polymer as described above into an aqueous or aqueous/organic composition which contains from 0.1% to 50% by weight of at least one therapeutic agent and/or excipient.

Still another aspect of the present invention is the provision of a method for the topical treatment of the skin, which comprises applying a composition as defined above to the skin, face or scalp of a human being or other mammal in need of such treatment. The type of treatment will depend on the active ingredient(s) dissolved or suspended in the composition. For example the composition may comprise a barrier cream, a facial moisturizer cream or lotion, a facial cleanser, a hand and body lotion, a spray moisturizer, a UV sun screening cream or lotion, a "sunless" tanning cream or lotion, a skin bleaching cream or lotion, a depilatory cream or lotion, a hair conditioning cream or lotion, a hair dyeing cream or lotion, a pre- or aftershave cream, lotion or gel, a disinfectant cream, lotion, ointment or gel, a soothing cream or lotion for sunburn, etc.

Other aspects of the present invention will become apparent from the following discussion and the examples. The examples merely illustrate certain aspects of the invention and are not intended to be limiting thereof.

DETAILED DESCRIPTION OF THE INVENTION

The hydrophilic, water swellable acrylic-based liquid dispersion polymer compositions employed in the present invention may be either anionic or cationic. Said polymers may be homopolymers or copolymers. They are formed from one or more monoethylenically unsaturated monomers that are either water soluble anionic or cationic monomers or from a predominantly anionic or cationic blend of monomers that may consist of anionic and cationic monomers or may consist of a mixture of anionic and/or cationic monomers and a minor amount of nonionic monomers.

The polymers may conveniently be obtained in the form of microparticles having an average particle size in the range of 0.1–2 microns by reverse phase emulsion polymerization of suitable monomers in a hydrophobic liquid, i.e. a liquid which has sufficiently low miscibility with water that it can be used as the non-aqueous phase in a reverse phase polymerization. The liquid must have substantially no solvating effect for the polymer, or for the monomers from which it is formed, throughout the range of temperatures at which the polymer is likely to be synthesized (for instance from 15 to 100° C.), since a solvating medium would be unsatisfactory for reverse phase emulsion polymerization. Likewise, the monomer or monomer blend must be water soluble to enable reverse phase polymerization to be carried out.

Suitable anionic monomers include acrylic acid, methacrylic acid and their alkali metal and ammonium salts, 2-acrylamido-2-methyl-propanesulfonic acid and its salts, sodium styrene sulfonate and the like. Acrylic acid is the most preferred anionic monomer. Preferably the carboxylic acid groups are at least 50%, advantageously 65–85% in the form of an alkali metal salt or ammonium salt, especially the sodium salt.

Suitable cationic monomers include diallyl dialkyl monomers such as diallyl dimethyl ammonium chloride, but preferably the cationic monomer is a dialkylaminoalkyl (meth)acrylate or -acrylamide. Although the polymer can be in free base form, especially when it is a cationic acrylamide or methacrylamide, it is preferably in the form of an acid addition or quaternary ammonium salt.

When the monomer is a cationic acrylamide or methacrylamide, the dialkylaminoalkyl group is generally a dialkylamino propyl or dialkylamino isopropyl group. When the monomer is a cationic acrylate or methacrylate, the dialkylaminoalkyl group is generally a dialkylaminoethyl group.

It is usually preferred for the cationic monomer to be a dialkylaminoalkyl (meth)acrylate acid salt or quaternary ammonium salt, most preferably dimethylaminoethyl methacrylate. Usually it is present as the methyl chloride quaternary ammonium salt.

Suitable nonionic monomers include acrylamide, methacrylamide, N-vinyl pyrrolidone and water soluble hydroxy-substituted acrylic or methacrylic esters.

If a cationic blend is used, the amount of cationic monomer is preferably more than 50% by weight of the blend, and usually it is at least 70% or at least 80% by weight of the blend. The preferred cationic polymers are formed wholly from cationic monomers.

If an anionic blend is used, the amount of anionic monomer is preferably more than 60% by weight of the blend, and usually it is at least 80% by weight of the blend. The preferred anionic polymers are formed wholly from anionic monomers.

The liquid dispersion polymer compositions are advantageously crosslinked by incorporating a small amount of a suitable crosslinking agent such as a polyfunctional vinyl addition monomer into the polymerization mixture. Preferably a water soluble crosslinking agent is used.

Any of the conventional polyethylenically unsaturated cross linking agents which are soluble in the monomer or monomer blend can be used, including materials which are di-, tri- or tetraethylenically unsaturated. Preferred are diethylenically unsaturated compounds such as methylene bis acrylamide, ethylene glycol di(meth) acrylate, di (meth) acrylamide, vinyloxyethylacrylate or -methacrylate and the like. Methylene bis acrylamide is the most preferred crosslinking agent.

The amount of cross linking agent is generally in the range from 100 to 10,000 parts by weight of cross linking agent per million parts (by dry weight) of monomer. Most preferably it is around 500 to 2000 ppm, especially 500 to 900 ppm for either cationic or anionic monomers. Optimum amounts can be determined by routine experimentation.

Especially preferred polymers for use in the present invention are the anionic polymer dispersed in Salcare® SC91 and the cationic polymers dispersed in Salcare® SC92 and Salcare® SC95 liquid dispersion polymers.

The hydrophilic polymers are prepared by reverse phase emulsion polymerization of hydrophilic monomers, preferably one or more acrylate and/or methacrylate monomers, in a hydrophobic liquid phase. Reverse phase emulsion polymerization is a well known technique which is described for example in U.S. Pat. No. 4,628,078, the disclosure of which is incorporated by reference in its entirety.

The continuous phase for the preparation of the instant liquid dispersion polymer compositions is provided at least in part by a liquid hydrophobic di- or triglyceride. Since the liquid dispersion polymer compositions are primarily intended for cosmetic or pharmaceutical purposes, liquid di- or triglycerides which are cosmetically and/or pharmaceutically acceptable and which are sufficiently hydrophobic to be useful as the continuous phase in a reverse phase polymerization are preferably used as the continuous phase. Many such materials are known and are commercially available. They can be natural or synthetic in origin. Naturally occurring triglycerides include, without limitation, fish liver oils such as cod liver oil, emu oil, palm oil, palm kernel oil, coconut oil, castor oil, olive oil, peanut oil, safflower oil, sunflower seed oil, rape seed oil, canola oil, corn oil, soybean oil, jojoba oil, macadamia oil, avocado oil, rice bran oil, evening primrose oil, grape seed oil, sweet almond oil, walnut oil, sesame oil, tall oil, cottonseed oil, apricot kernel oil, wheat germ oil, meadowfoam seed oil, borage seed oil, linseed oil and cashew oil. Synthetic di- and/or triglycerides may be prepared by esterifying glycerin with appropriate fatty acids by methods known per se.

A particularly preferred naturally occurring triglyceride is soybean oil. Soybean oil has been used for many years in food and beverages. It is known to contain high levels of the triglycerides of oleic and linoleic fatty acids. Their presence in the resulting thickened aqueous compositions gives formulations containing them good spreading properties, with superior emolliency characteristics compared to mineral oil and other synthetic oils. Since soybean oil is polar, it reduces the surface tension of the skin and can penetrate further into the stratum corneum, giving increased skin moisturization, but providing a less occlusive feel on the skin. In addition, the triglycerides break down naturally in the skin to give a combination of the fatty acids and glycerin.

The amount of the hydrophobic liquid phase used in the polymerization is dictated primarily by the need to provide a satisfactory reverse phase emulsion medium. This would generally be at least about 1 part by weight of the di- or triglyceride per part by weight of the hydrophilic polymer (dry weight). In order to obtain liquid dispersion polymer compositions having higher amounts of the microparticles in the oil, for example from 1.2 to about 1.7 parts by weight of the hydrophilic polymer (dry weight) in the di- or triglyceride, as well as to facilitate processing, it is expedient to employ a volatile inert hydrophobic solvent. Suitable inert hydrophobic solvents include hydrocarbons and halogenated hydrocarbons.

One particularly preferred hydrocarbon mixture is Isopar G from Exxon. Conveniently 1 to 2 parts, preferably 1.3 to 1.9 parts of the volatile inert hydrophobic solvent per part of the hydrophilic polymer on a dry weight basis is employed.

The polymer is prepared by conventional reverse phase emulsion procedures, namely by adding 1 part by weight (dry weight) of at least one aqueous ethylenically unsaturated monomer, optionally including a sequesterant and a crosslinking diethylenically unsaturated monomer, into about 1 to 3 parts by weight of a hydrophobic liquid comprising at least in part a liquid hydrophobic di- or triglyceride and containing about 0.1 to 0.2 parts of at least one conventional water-in-oil emulsifier having a HLB value below 9.0 and optionally 0.1 to 0.2 parts of a polymeric stabilizer surfactant, with intensive agitation so as to form a substantially stable emulsion of the required fine particle size. Suitable water-in-oil emulsifiers are well known to those skilled in the art. Sorbitan esters such as sorbitan monooleate and ethoxylated sorbitan esters such as Tween 81 from ICI are preferred, with mixtures thereof being especially preferred. Diethylenetriamine pentaacetic acid, sodium salt is a suitable sequesterant.

The reaction mixture is purged with nitrogen and polymerization is initiated by addition of a conventional source of free radicals. Suitable polymerization initiators are well known to those skilled in the art. Typical free radical-forming catalysts include peroxygen compounds such as sodium, potassium and ammonium persulfates, caprylyl peroxide, benzoyl peroxide, hydrogen peroxide, pelargonyl peroxide, cumene hydroperoxide, tertiary butyl diperphthalate, tertiary butyl perbenzoate, sodium peracetate, di(2-ethylhexyl)peroxydi-carbonate, and the like, as well as azo catalysts such as azodiisobutyronitrile. Other useful catalysts are the heavy metal-activated catalyst systems. A preferred type of polymerization initiator is a redux initiation pair. After initiation appropriate temperature and agitation conditions are maintained until the conversion of the monomer to polymer is substantially complete. Appropriate conditions are well known to those of ordinary skill in the art.

The water and any volatile solvent are then removed from the reverse phase emulsion, for example by distillation under reduced pressure, so as to produce a substantially anhydrous stable dispersion of polymer particles less than 2 microns in size dispersed in the di- or triglyceride.

About 0.5% to 8% by weight, based on the weight of the composition, preferably from 1% to 3% by weight of a nonionic oil-in-water emulsifier having a HLB generally above 10 is added after distillation is complete. Suitable emulsifiers of this type are well known to those skilled in the art. Ethoxylated alcohols are preferred, with PPG1-trideceth 6 being especially preferred.

It is a further feature of the invention that a suitable amphipathic "stabilizer" surfactant is employed as a processing aid to maintain emulsion integrity through the distillation process and to provide for the final liquid polymer dispersion to be a free flowing liquid, even when it contains high levels of microparticles of the water soluble or swellable dispersed polymer. Advantageously 0.02 to 0.3 parts, especially 0.1 to 0.2 parts of this stabilizer surfactant is employed per part by weight (dry weight) of the ethylenically unsaturated monomer.

A preferred amphipathic stabilizer surfactant is a polymer which is a reaction product of poly-12-hydroxystearic acid, glycidyl methacrylate and methacrylic acid.

U.S. Pat. No. 4,075,141 mentions a dispersion stabilizer for polymeric microparticles useful for coatings (i.e. paint) compositions, which comprises a solution of a reaction product of 50.3% glycidyl methacrylate, 0.9% methacrylic acid, and 49.5% of a reaction product of 89.2% poly-12-hydroxystearic acid and 10.8% glycidyl methacrylate.

The preferred amphipathic stabilizer surfactant of the present invention is very different, being a polymer comprising a reaction product of 60 to 80% by weight of poly-12-hydroxystearic acid, 10% to 20% of glycidyl methacrylate and 5% to 25% by weight of methacrylic acid.

The inventive polymer of poly-12-hydroxystearic acid, glycidyl methacrylate and methacrylic acid may be prepared as follows.

Poly-12-hydroxystearic acid is known per se. It is conveniently obtained by acid-catalyzed intermolecular condensation of 12-hydroxystearic acid in a refluxing inert solvent which forms an azeotrope with water, for example an aliphatic or aromatic hydrocarbon such as Isopar G. Commercially available 12-hydroxystearic acid contains non-hydroxylated fatty acids, mostly stearic acid, as impurities. These impurities terminate the self-condensation reaction, generally limiting the molecular weight that can be achieved to about 2000. Poly-12-hydroxystearic acid having a molecular weight between 1000 and 2000 is suitable for use in the inventive polymers. Poly-12-hydroxystearic acid having a molecular weight of about 1500 is preferred.

Poly 12-hydroxystearic acid (1 part) is then reacted with 1 to 2 parts by weight of glycidyl methacrylate at a temperature of 100 to 180° C., preferably 120 to 160° C., in an inert solvent, for example a hydrocarbon solvent like Isopar G, in the presence of a basic catalyst and a small amount, for example 0.8 to 1% of paramethoxyphenol. A preferred basic catalyst is about 1% by weight, based on the glycidyl methacrylate, of cocodimethylamine.

A mixture comprising 75 to 95 parts by weight of the product of this reaction, conveniently as about a 70% solution in the hydrocarbon solvent, is then combined with 5 to 25 parts by weight of methacrylic acid and then reacted at 70 to 110° C. in the presence of about 1% based on the total weight of the reactants of an azo free radical addition polymerization catalyst. Vazo 67 is particularly preferred. The resulting product is useful as a stabilizer surfactant in the preparation of liquid dispersion polymer compositions.

On stirring an inventive liquid dispersion polymer into an aqueous or water-containing system, the activator surfactant converts the hydrophobic carrier into an oil-in-water emulsion. At the same time the hydrophilic polymer expands on exposure to water but does not dissolve, resulting in a smooth and rapid viscosity increase. Typically the polymer particles swell to give a microparticulate thickening system comprising polymer particles having a typical particle size in the range of 2.5–5 microns in diameter. As with the previously known Salcare® liquid dispersion polymers, since the water molecules move into the small polymer particles by osmosis, the osmotic effect experienced by the polymer particle is a balance between water and any electrolyte present in the system. Hence high electrolyte levels reduce the swelling of the polymer particles.

The inventive liquid dispersion polymer compositions provide microparticulate thickening systems which give effective thickening to aqueous or aqueous/organic formulations at concentrations of 0.1% to 8%, preferably 1% to 6%, by weight. In addition however they combine the thickening effect of the liquid dispersion polymer with the advantages of the di- or triglyceride carrier oil.

As previously indicated, the liquid dispersion polymer compositions are compatible with a wide variety of personal care active ingredients and auxiliaries. The formulation examples below merely illustrate a few representative aspects of the formulating possibilities and are not intended to be limiting in any way. Salcare® AST is the designation of the most particularly preferred composition wherein the polymer in the liquid dispersion polymer comprises microparticles of a water swellable polyacrylic acid polymer wherein about 75% of the acid groups are in the form of their sodium salt, and wherein the triglyceride oil comprises soybean oil.

All percents are percent by weight of the formulation. Viscosities are determined with a Brookfield viscometer.

EXAMPLE 1

Jojoba And Sunflower Oil Cream

| | Trade Name | Supplier | INCI Name | % |
|---|---|---|---|---|
| 1 | | | Aqua | to 100 |
| 2 | Salcare AST | Ciba Specialty Chemicals | Sodium Acrylates Copolymer (and) Glycine Soja (and) PPG-1 Trideceth-6 | 3.00 |
| 3 | Jojoba Oil | A&E Connock | Buxus Chinensis | 5.00 |
| 4 | FloraSun-90 | Chesham Chemicals | Helianthus Annus | 5.00 |
| 5 | Sweet Almond Oil | A&E Connock | Prunus Dulcis | 5.00 |
| 6 | Dow Corning 245 | Dow Corning | Cyclomethicone | 5.00 |
| 7 | Nipastat Sodium | Nipa Laboratories | Sodium Methylparaben (and) Sodium Propylparaben (and) Sodium Ethylparaben (and) Sodium Butylparaben | 0.10 |
| 8 | Uvinul MS-40 | BASF | Benzophenone-4 | 0.15 |
| 9 | | Fragrance Oils International | Parfum | 0.10 |
| 10 | | Ciba Specialty Chemicals | Color | qs |

Method:
1) Weigh (1) into a clean dry beaker and add each of the ingredients except (2) in turn, stirring between additions.
2) increase stirrer speed and add (2), continuing to stir until viscous and homogeneous.
Typical Properties:
Appearance: smooth viscous cream
Viscosity: 30,000–40,000 cPs
pH: 6.0–6.5.

Typical Properties:

Appearance: smooth viscous cream

Viscosity: 30,000–40,000 cPs pH: 6.0–6.5.

EXAMPLE 2

Skin Firming Cream

| | Trade Name | Supplier | INCI Name | % |
|---|---|---|---|---|
| 1 | | | Aqua | to 100 |
| 2 | Salcare AST | Ciba Specialty Chemicals | Sodium Acrylates Copolymer (and) Glycine Soja (and) PPG-1 Trideceth-6 | 3.50 |
| 3 | Hydroveg UV | Paroxite | Aqua (and) Hydrolysed Wheat Protein (and) Urea (and) Sorbitol (and) Lysine PCA (and) Allantoin (and) Diglycerin (and) Lactic Acid (and) Sodium PCA | 3.75 |
| 4 | Dermol 89 | Paroxite | Octyl Isononanoate | 3.75 |
| 5 | Dermogene | Paroxite | Aqua (and) Propylene Glycol (and) Hydrolysed Soy Protein | 1.00 |
| 6 | Titrated Raspberry Extract | Paroxite | Rubus Idaeus | 0.25 |
| 7 | Aloe Vera | S. Black | Aloe Barbadensis | 0.50 |
| 8 | Fragrance | Fragrance Oils International | Parfum | 0.35 |
| 9 | Tinosorb OMC | Ciba Specialty Chemicals | Octyl Methoxycinnamate | 1.50 |
| 10 | Nipaguard BPX | Nipa Laboratories | Phenoxyethanol (and) Methylparaben (and) Propylparaben (and) 2-Bromo-2-Nitropropane-1,3-Diol | 0.15 |

Method:
1) Weigh (1) into a clean, dry beaker and add all ingredients except (2) in turn, stirring between additions.
2) Increase stirrer speed and add (2), continuing to stir until smooth and viscous.
Typical Properties
Appearance: smooth, viscous cream
Viscosity: 20,000–25,000 cPs
pH: 6.0–6.5.

EXAMPLE 3

High SPF Sunscreen

| | Trade Name | Supplier | INCI Name | % |
|---|---|---|---|---|
| 1 | | | Aqua | to 100 |
| 2 | Salcare AST | Ciba Specialty Chemicals | Sodium Acrylates Copolymer (and) Glycine Soja (and) PPG-1 Trideceth-6 | 3.00 |
| 3 | Tinosorb OMC | Ciba Specialty Chemicals | Octyl Methoxycinnamate | 7.50 |
| 4 | Tinosorb B3 | Ciba Specialty Chemicals | Benzophenone-3 | 6.00 |
| 5 | Uvinul N539 | BASF | Octocrylene | 9.00 |
| 6 | Dow Corning 200 | Dow Corning | Dimethicone | 2.00 |
| 7 | Dow Corning 1403 | Dow Corning | Dimethicone (and) Dimethiconol | 5.00 |
| 8 | Fragrance | Fragrance Oils International | Parfum | 0.35 |
| 9 | Phenonip | Nipa Laboratories | Phenoxyethanol (and) Methylparaben (and) Butylparaben (and) Ethylparaben (and) |  0.30 |

-continued

High SPF Sunscreen

| | Trade Name | Supplier | INCI Name | % |
|---|---|---|---|---|
| 10 | Germall 115 | ISP | Propylparaben Imidazolidinyl Urea | 0.20 |
| 11 | | | Alcohol Denat. | 5.00 |
| 12 | Volpo TS | Croda Chemicals | Trideceth-5 | 2.50 |

Method:
1) Weigh (1) into a clean, dry beaker and add all ingredients except (2) in turn, stirring between additions.
2) Increase stirrer speed and add (2), continuing to stir until smooth and viscous.
Typical Properties
Appearance: smooth, viscous flowable lotion
Viscosity: 10,000–15,000 cPs
pH: 6.5–7.0.

What is claimed is:

1. A liquid dispersion polymer composition comprising a hydrophilic, water soluble or swellable polymer obtained by reverse phase emulsion polymerization which is dispersed in a di- or triglyceride oil containing an oil-in-water surfactant and a polymeric surfactant which comprises a reaction product of poly-12-hydroxystearic acid, glycidyl methacrylate and methacrylic acid, and wherein the polymer is in the form of microparticles having an average particle size in the range of 0.1 to 2 microns.

2. A liquid dispersion polymer composition according to claim 1, which comprises
   a) from 35% to 65% by weight of the polymer,
   b) from 20% to 50% by weight of a di- or triglyceride oil and
   c) from 5% to 25% by weight of the surfactant mixture, each based on the total weight of the composition.

3. A liquid dispersion polymer composition according to claim 1, which comprises
   a) from 40% to 60% by weight of the polymer, wherein the polymer is anionic or cationic and is water swellable,
   b) from 25% to 45% by weight of a di- or triglyceride oil, and
   c) from 8% to 20% by weight of the surfactant mixture, each based on the total weight of the composition.

4. A liquid dispersion polymer composition according to claim 3, which comprises
   a) from 45% to 58% by weight of the water swellable polymer, wherein the polymer is anionic or cationic and is water swellable,
   b) from 30% to 40% by weight of a di- or triglyceride oil, and
   c) from 10% to 18% by weight of the surfactant mixture, each based on the total weight of the composition.

5. A liquid dispersion polymer composition according to claim 3, which comprises
   a) from 45% to 58% by weight of the water swellable polymer, wherein the polymer is anionic and 65% to 85% of the acid groups are in the form of their sodium salt,
   b) from 32% to 38% by weight of a triglyceride oil, and
   c) from 12% to 18% by weight of the surfactant mixture, each based on the total weight of the composition.

6. A liquid dispersion polymer composition according to claim 1, wherein the hydrophilic polymer is cationic and is sufficiently cross-linked to swell but not dissolve in water.

7. A liquid dispersion polymer composition according to claim 1, wherein the polymer is anionic and is sufficiently cross-linked to swell but not dissolve in water.

8. A liquid dispersion polymer composition according to claim 5, wherein the anionic polymer is polyacrylic acid which is crosslinked with 500 to 2000 ppm of a water soluble crosslinking agent.

9. A liquid dispersion polymer composition according to claim 8, wherein the water soluble crosslinking agent is methylene bis acrylamide.

10. A liquid dispersion polymer composition according to claim 1, wherein the hydrophilic polymer is prepared by reverse phase emulsion polymerization of one or more acrylate and/or methacrylate monomers in a hydrophobic liquid phase which comprises at least one di- or triglyceride oil.

11. A liquid dispersion polymer composition according to claim 1, wherein the di- or triglyceride oil is a cosmetically and/or pharmaceutically acceptable oil of natural or synthetic origin.

12. A liquid dispersion polymer composition according to claim 1, wherein the di- or triglyceride oil is selected from the group consisting of fish liver oils, emu oil, palm oil, palm kernel oil, coconut oil, castor oil, olive oil, peanut oil, safflower oil, sunflower oil, rape seed oil, canola oil, corn oil, soybean oil, jojoba oil, macadamia oil, avocado oil, rice bran oil, evening primrose oil and cashew oil.

13. A liquid dispersion polymer composition according to claim 12, wherein the oil is soybean oil.

14. A thickened aqueous or water-containing composition which comprises
   a) 0.1% to 8% by weight of a liquid dispersion polymer composition according to claim 1,
   b) 0.1% to 50% by weight of additional ingredients, and
   c) 45% to 99% of water or a mixture of water and a water-miscible organic solvent.

15. A thickened aqueous or water-containing composition according to claim 14, which is in the form of a lotion, cream, salve, gel or ointment.

16. A thickened aqueous or water-containing composition which comprises
   (a) 0.1% to 8.0% by weight of a liquid dispersion polymer composition comprising a hydrophilic, water soluble or swellable polymer obtained by reverse phase emulsion polymerization which is dispersed in a di or triglyceride oil and an oil-in-water surfactant, wherein the polymer is in the form of microparticles having an average particle size in the range of 0.1 to 2 microns,
   (b) 0.1% to 50% by weight of a cosmetic or pharmaceutical excipient and/or active ingredient, and
   (c) 45% to 99% by weight of water or a mixture of water and a water miscible organic solvent.

17. A thickened aqueous or water-containing composition according to claim 16, wherein the additional ingredient b) is a cosmetic excipient and/or active ingredient selected from the group consisting of antimicrobials, acetylated lanolin alcohol, allantoin, aloe vera, acetamide monoethanolamine, myrstyl propionate, dimethicone copolyol, dimethyl polysiloxane, moisturizers, barrier creams, emollients, alpha hydroxy acids, hair conditioners, perfume components, hair dyes and bleaches, UV sun screening agents, "sunless" tanning agents, whitening agents, insect repellents, essential oils, vitamins, and preservatives, or is a pharmaceutical excipient and/or active ingredient selected from the group consisting of substances which treat itching, tingling, scaling, inflammation or infection of the skin, burns, and scalp hair loss.

18. A method for the preparation of a therapeutic lotion, cream, salve, gel or ointment which comprises mixing 0.1% to 8% by weight of a liquid dispersion polymer into an aqueous or aqueous/organic composition which contains from 0.1% to 50% by weight of at least one therapeutic agent and/or excipient, said liquid dispersion polymer comprising a hydrophilic, water soluble or swellable polymer obtained by reverse phase emulsion polymerization which is dispersed in a di or triglyceride oil and an oil-in-water surfactant, wherein the polymer is in the form of microparticles having an average particle size in the range of 0.1 to 2 microns.

19. A method for the therapeutic topical treatment of the skin, which comprises applying a composition as defined in claim 16 to the skin, face or scalp of a human being or other mammal in need of such treatment.

20. A liquid dispersion polymer composition according to claim 1, comprising a hydrophilic, water soluble or swellable polymer obtained by reverse phase emulsion polymerization which is dispersed in a di- or triglyceride oil containing an oil-in-water surfactant and a polymeric surfactant which comprises a reaction product of 60 to 80% by weight of poly-12-hydroxystearic acid, 10% to 20% of glycidyl methacrylate and 5% to 25% by weight of methacrylic acid, and wherein the polymer is in the form of microparticles having an average particle size in the range of 0.1 to 2 microns.

* * * * *